US012751998B2

(12) United States Patent
Record et al.

(10) Patent No.: US 12,751,998 B2
(45) Date of Patent: Oct. 6, 2026

(54) SYSTEMS AND METHODS FOR ADMINISTERING DERMAL AND TRANSDERMAL IMMUNOTHERAPY TOPICAL APPLICATION COMPOUNDS TO ANIMALS

(71) Applicant: Allibre Animal LLC, Austin, TX (US)

(72) Inventors: Robert A. Record, Austin, TX (US); David Faulkner, Austin, TX (US); Survam Patel, Austin, TX (US)

(73) Assignee: Allibre Animal LLC, Austin, TX (US)

( * ) Notice: Subject to any disclaimer, the term of this patent is extended or adjusted under 35 U.S.C. 154(b) by 776 days.

(21) Appl. No.: 18/117,559

(22) Filed: Mar. 6, 2023

(65) Prior Publication Data

US 2023/0292707 A1 Sep. 21, 2023

Related U.S. Application Data

(60) Provisional application No. 63/320,399, filed on Mar. 16, 2022.

(51) Int. Cl.

| | |
|---|---|
| ***A61K 39/00*** | (2006.01) |
| ***A61D 7/00*** | (2006.01) |
| ***A61K 39/35*** | (2006.01) |

(52) U.S. Cl.

CPC ................ *A61K 39/00* (2013.01); *A61D 7/00* (2013.01); *A61K 39/35* (2013.01); *A61B 2503/40* (2013.01); *A61K 2039/54* (2013.01); *A61M 2210/0662* (2013.01)

(58) Field of Classification Search

None

See application file for complete search history.

(56) References Cited

FOREIGN PATENT DOCUMENTS

| | | |
|---|---|---|
| WO | WO 2002/093998 * | 11/2002 |
| WO | 2017060774 A1 | 4/2017 |

OTHER PUBLICATIONS

Gao et al. 'Kampo Medicines for Mite Antigen-Induced Allergic Dermatitis in NC/Nga Mice.' eCAM 2005;2(2)191-199 doi:10.1093/ecam/neh077.*

"Atopic Dermatitis in Dogs" https://veterinarypartner.vin.com/doc/?id=4951973&pid=19239 The VIN Dermatology Consultants, retrieved on Nov. 18, 2021, 2 pages.

"Methimazole Administration to Cats: In Vivo and In Vitro Studies of Transdermal Absorption", Doctor or Philosophy in Veterinary Science, Massey University, Manawatu, New Zealand, Kate Edwina Hill, 2015, 380 pages.

Mary Morris, M.D. et al., "Sublingual Immunotherapy for Pets: A Gide for Veterinary Dermatologists", Allergy associates of La Crosse, La Crosse, WI and School of Veterinary Medicine, University of Wisconsin, Madison, WI, 7 pages.

* cited by examiner

*Primary Examiner* — Nora M Rooney
(74) *Attorney, Agent, or Firm* — Baker Botts L.L.P.

(57) ABSTRACT

Systems and methods for detecting that the animal has the allergy condition, determining a first quantity of a topical application medium and a first quantity of an allergen based at least in part on one or more attributes of the animal, providing a first topical application compound, the first topical application compound comprising the first quantity of the allergen and the first quantity of the topical application medium, and applying the first topical application compound to one or more ears of the animal one or more times to treat the allergy condition.

14 Claims, 4 Drawing Sheets

SYSTEMS AND METHODS FOR ADMINISTERING DERMAL AND TRANSDERMAL IMMUNOTHERAPY TOPICAL APPLICATION COMPOUNDS TO ANIMALS

CROSS-REFERENCE TO RELATED APPLICATIONS

The present disclosure claims priority to and the benefit of Provisional Patent Application Ser. No. 63/320,399, entitled "Systems and Methods for Administering Dermal and Transdermal Immunotherapy Topical Application Compounds to Animals," filed on Mar. 16, 2022, the entire disclosure of which is herein incorporated by reference.

FIELD OF THE INVENTION

The present disclosure relates to a system and methods for providing a more psychologically benign method of administering allergy medication to animals for whom traditional medication administration methods are unsuitable (for example and without limitation, needle-phobic animals), or more specifically to an immunotherapy method whereby allergens are administered to dogs and cats dermally or transdermally via a topical application compound such as a cream, gel, or oil.

BACKGROUND

Existing methods of immunotherapy are unsuitable for many household pets. Allergen-specific immunotherapy (commonly referred to as AIT) is accomplished by introducing small amounts of an allergen in a controlled manner until the patient becomes desensitized to the allergen. For dogs and cats, the primary manner by which allergens are introduced is via subcutaneous immunotherapy, in which a needle injects the allergen under the skin. It is not uncommon for dogs and cats to be afraid of needles. This fear can cause otherwise friendly dogs and cats to become uncooperative or aggressive, thereby impeding administration of the medication and creating a danger to any nearby veterinarians, veterinary technicians, or owners, as well as the animal. Further, this fear can cause the dog or cat to form a negative association with medical care. Beyond making administration of medication more cumbersome, inefficient, and dangerous, some patients feel that a pet's negative association with medical care may adversely affect the human-animal bond in the home environment.

Sublingual immunotherapy has been used as an alternative to subcutaneous immunotherapy, but it is problematic for many owners and animals. Sublingual immunotherapy is practiced by administering oral-glycerinated allergens to the oral cavity, typically under the tongue. Though sublingual immunotherapy boasts similar efficacy to subcutaneous immunotherapy when practiced correctly, it is impeded by four barriers to correct administration. First, sublingual immunotherapy is hampered by a lesser version of the same major drawback as subcutaneous immunotherapy—that is, it is common for animals to be averse to having medication placed underneath their tongues, and this aversion can create a negative association with medical care. Second, sublingual immunotherapy generally requires two daily administrations, which can be difficult for clients with schedules that conflict with the requisite administration timing. Third, food and water must be restricted for up to thirty minutes to prevent interference with the absorption of allergens. Fourth, the efficacy of sublingual immunotherapy is severely impeded if the animal swallows the allergens before the allergens are sufficiently absorbed across the mucous membranes. In short, sublingual immunotherapy serves as a substitute to subcutaneous immunotherapy for animals in some cases, but both methods are ill-suited to a significant percentage of dogs and cats.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features.

Figure 1:
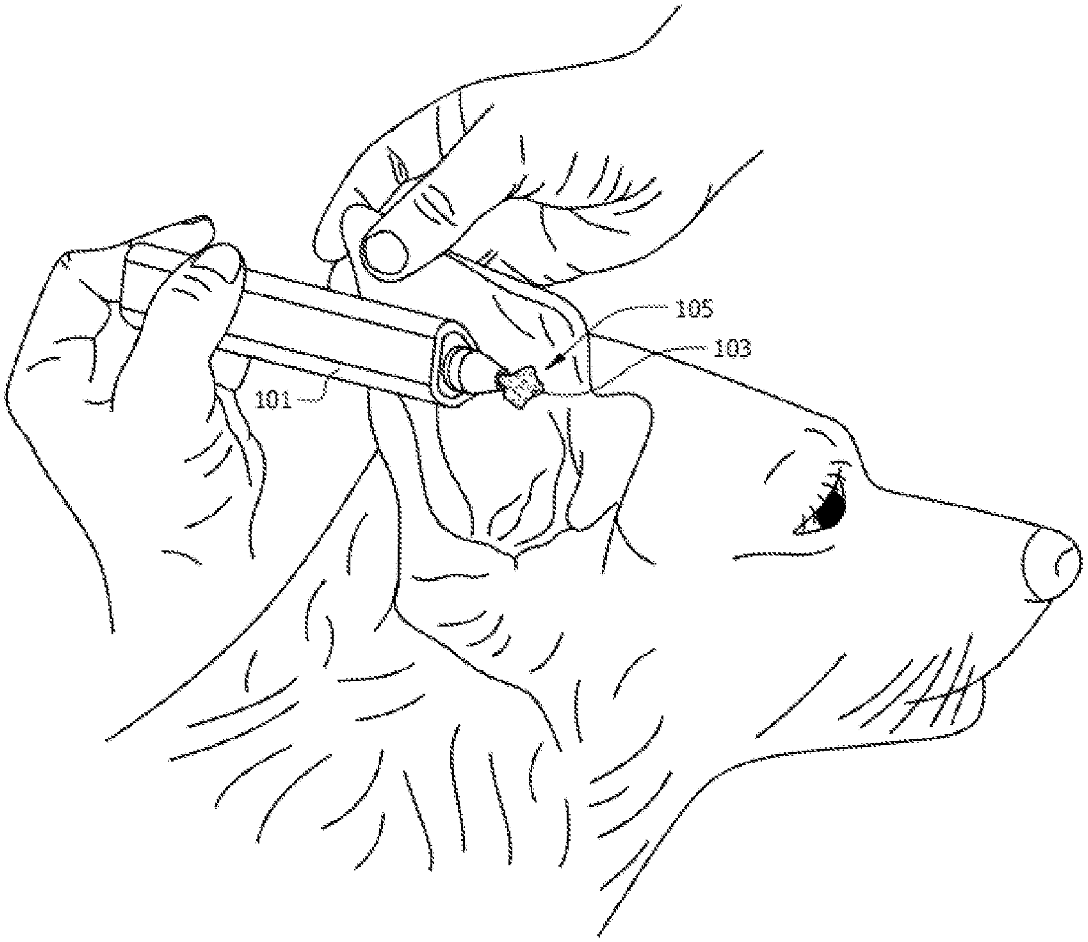
FIG. 1 depicts an exemplary illustration of an immunotherapy topical application compound being applied transdermally to the pinna of a dog's ear, according to one or more aspects of the present disclosure.

While embodiments of this disclosure have been depicted and described and are defined by reference to exemplary embodiments of the disclosure, such references do not imply a limitation on the disclosure and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only and are not exhaustive of the scope of the disclosure.

DETAILED DESCRIPTION

The present disclosure relates to a system and methods for providing a more psychologically benign method of administering allergy medication to animals for whom traditional medication administration methods are unsuitable (for example and without limitation, needle-phobic animals), or more specifically to an immunotherapy method whereby allergens are administered to dogs and cats dermally or transdermally via a topical application compound.

Described herein is a technique for administering a dermal or transdermal immunotherapy topical application compound to animals. The disclosed methods and systems may be practiced by administering a small amount of an allergen dispersed into a cream, gel, or oil to either (1) the pinna of an animal's ear; or (2) another location on an animal's skin at which the topical application compound is unlikely to be rubbed or licked away. The allergen may be diluted into a diluent (for example and without limitation, one or more of human serum albumin (HSA), sterile water, sterile water with phenol, or 50% glycerin) via any known technique for medication dilution, including and without limitation by creating serial dilutions based on the animal's weight. In one or more embodiments, the produced medication may then be mixed into a topical application medium, for example and without limitation, an oil-in-water cream, a water-in-oil cream, a gel, or an oil. Finally, the topical application compound may be applied regularly to the pinna of the animal's ear or another location on the animal's skin at which the topical application compound is unlikely to be rubbed or licked away. In one or more embodiments, one or more of the concentration and the dosage of the topical application compound may be increased at regular time intervals until a maintenance concentration and dosage are reached. Those skilled in the art may find it desirable to apply the topical application compound daily, though any practical time interval of administration falls within the scope of the invention. The present invention allows a small amount of allergen introduced dermally or transdermally to the immune system of an animal via the topical application compound to desensitize the animal to the allergen. In this way, an animal's immunologic response to an allergen may be lessened over time until the animal is no longer allergic to the allergen.

The terms "topical application compound," "topical application medium," and the plural forms of those terms are used herein as umbrella terms for pharmaceutical bases by which allergens may be applied to the skin of an animal for absorption to the immune systems, including and without limitation all forms of creams, gels, and oils whether administered dermally or transdermally; the terms "topical application compound," "topical application medium," and the plural forms of those terms should be understood to include combinations comprising (1) one or more media and one or more allergen and (2) one or more media without an allergen yet inserted. The terms "dog" and "dogs" are used herein to mean any one or more canines owned, domesticated, or cared for by one or more humans. Similarly, the terms "cat" and "cats" are used herein to mean any one or more felines owned, domesticated, or cared for by one or more humans. The terms "owner" and "owners" are used herein to mean one or more owners of one or more animals. The term "transdermal" and derivatives thereof is used herein to mean administration to one or more pinnae of one or more animal's ears. The terms "dermal," "topical," and derivatives thereof are used herein to mean administration to one or more animal's skin; these terms are broader than "transdermal," and they apply to application to the skin of the pinna of the ear as well as any other location on the skin.

In one or more aspects of the present disclosure, a veterinarian, veterinary technician, researcher, or owner may utilize an information handling system to control one or more operations associated with the process of producing or administering one or more dermal or transdermal immunotherapy topical application compounds. An information handling system may include any system or mechanism by which information may be processed, stored, transmitted, copied, received, or otherwise handled. Examples of information handling systems include computers, smart devices, processors, network storage systems, or any other by which information may be handled. The information handling system may include one or more of a hard drive, random access memory (RAM), a processing system (for example and without limitation, a central processing unit (CPU)), read-only memory (ROM), a disk drive, a mechanism for communicating with external devices (including and without limitation via a the Internet, an intranet, or a local connection), and an input and/or output device (including and without limitation a mouse, a keyboard, or a display), including multiples of the preceding list (for example and without limitation, multiple input devices). In one or more embodiments, the information handling system may connect to external devices via one or more of a wired or wireless connection. In one or more embodiments, the information handling system may send one or more signals to control one or more pieces of hardware (for example and without limitation, a dispenser of emulsion cream).

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming but would nevertheless be a routine undertaking for those of ordinary skill in the art having the benefit of the present disclosure.

The present disclosure discloses several embodiments specific to atopic dermatitis. These embodiments are by way of example and not limitation. One skilled in the art and with the benefit of the present disclosure would understand that the disclosed systems and methods may be practiced to treat other indications. For example, and without limitation, the disclosed systems and methods may be practiced to treat and/or prevent any one or more of canine asthma, feline asthma, and feline atopic skin syndrome ("FAAS").

Throughout this disclosure, a reference numeral followed by an alphabetical character refers to a specific instance of an element and the reference numeral alone refers to the element generically or collectively. Thus, as an example (not shown in the drawings), widget "1a" refers to an instance of a widget class, which may be referred to collectively as widgets "1" and any one of which may be referred to generically as a widget "1". In the figures and the description, like numerals are intended to represent like elements.

To facilitate a better understanding of the present disclosure, the following examples of certain embodiments are given. In no way should the following examples be read to limit, or define, the scope of the disclosure. Embodiments of the present disclosure may be applicable to any system, process, or mechanism for one or more of diluting an allergen into a diluent, placing the diluent/allergen mix into a topical application medium, and applying the topical application compound dermally or transdermally to an animal. Embodiments described below with respect to one implementation are not intended to be limiting.

FIG. 1 depicts an exemplary illustration of an immunotherapy cream being applied transdermally to the pinna of a dog's ear, according to one or more aspects of the present disclosure. Though a dog's ear is depicted, FIG. 1 should be understood to apply to the ears of any animal. Further, FIG. 1 should be understood to apply to the ears or any other suitable location on an animal's skin for administration of an immunotherapy cream. Additionally, though a cream is depicted in FIG. 1, embodiments using any form of one or more topical application compounds (including and without limitation any cream, gel, or oil) are well within the scope of this disclosure.

In one or more embodiments, a topical application compound 103 (for example and without limitation, an emulsion cream mixed with an allergen) may be applied via an emulsion pen 101 transdermally to the pinna 105 of an animal's ear. In one or more embodiments, the topical application compound 103 may be applied by one or more of an emulsion pen 101, a micro-pen, a syringe, by hand, or via any other method of application. In one or more embodiments, the topical application compound 103 may be applied dermally to a suitable location. A location is suitable if (1) it is probable that the topical application compound will be absorbed into the skin (for example and without limitation, if the area of the skin is not unduly obscured by hair or fur) and (2) it is unlikely that the animal will rub, lick, or otherwise remove the topical application compound from the skin before the allergen has been absorbed into the immune system. An Elizabethan collar—that is, a cone-shaped, cylinder-shaped, or other configuration of a blocking material (including and without limitation plastic, fabric, cardboard, cloth, and fiber) used to surround one or more of an animal's head or neck to prevent the animal from licking, rubbing, or biting a part of its body—may be used to prevent the animal from rubbing, licking, or otherwise removing the topical application compound from the skin before the allergen has been absorbed into the immune system. In one or more embodiments, the topical application compound 103 may be applied to the pinna of the ear or a semi-hairless portion of the abdomen—this list is not meant to be exhaustive, and any suitable location is within the scope of this disclosure. In one or more embodiments, it may be desirable to alternate the application location, for example and without limitation, by administering a first dose to an animal's right pinna, a second dose to the animal's left pinna, and subsequent doses to alternating pinnae.

In one or more embodiments, a micro-pen or emulsion pen 101 may be used to administer the topical application compound 103 by rotating the pen 101 until it clicks. Each click, the pen 101 may dispense a quantity of topical application compound 103, for example and without limitation, 0.05 milliliters (mL). In one or more embodiments, the topical application compound 103 may then be gently rubbed into the application site 105. This rubbing may continue for any period sufficient to allow for absorption of the topical application compound 103, for example and without limitation, for five to ten seconds. In some embodiments, a veterinarian, veterinary technician, researcher, or owner may administer the topical application compound 103. In one or more embodiments, it may be desirable to administer the topical application compound regularly, for example and without limitation, once per day. Further, it may be desirable to steadily increase one or more of the concentration or quantity of the topical application compound 103 until a maintenance concentration is reached.

The present invention allows a small amount of allergen introduced through the skin to the immune system of the animal via the topical application compound 103 to desensitize the animal to the allergen. In this way, an animal's immunologic response to an allergen may be lessened over time until the animal is no longer allergic to the allergen. The invention may be used to treat one or more allergic conditions, for example and without limitation, atopic dermatitis.

Figure 2:
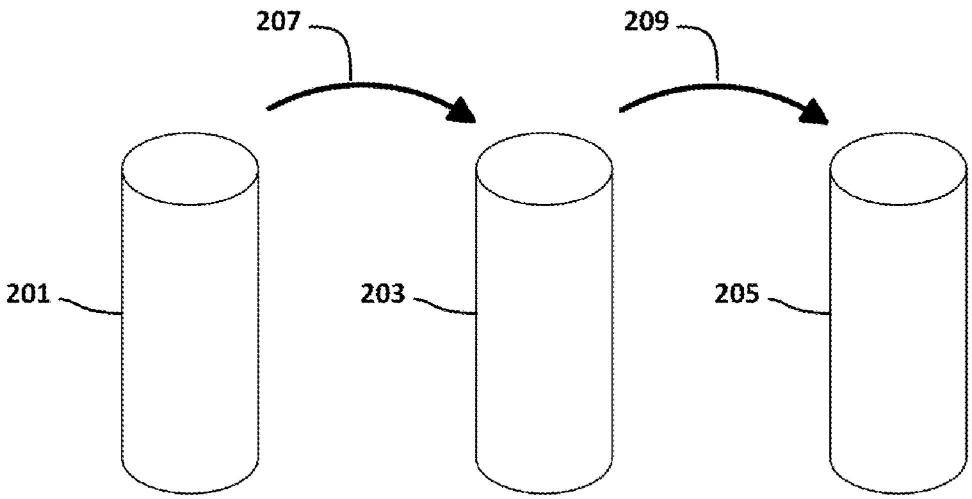
FIG. 2 depicts an exemplary diagram of a method for creating serial dilutions of an immunotherapy topical application compound, according to one or more aspects of the present disclosure.

FIG. 2 depicts an exemplary diagram of a method for creating serial dilutions of an immunotherapy cream, according to one or more aspects of the present disclosure. Though a cream is depicted in FIG. 2, embodiments using any form of one or more topical application compounds (including and without limitation any cream, gel, or oil) are well within the scope of this disclosure. FIG. 2 depicts three dilutions 201, 203, and 205; however, those skilled in the art will understand that any number of dilutions may be used without departing from the scope of the present disclosure. In one or more embodiments, a first dilution 201 may be formed via a mixture of an allergen and a diluent. The allergen should be the allergen to which an animal is allergic. The diluent may be any known diluent, including and without limitation HSA, sterile water, sterile water with phenol, 50% glycerin, or any combination therein. In one or more embodiments, a portion of the first dilution 201 may be transferred 207 to begin creation of a second dilution 203. Additional diluent may be added to the second dilution 203 to achieve a less concentrated dilution. In one or more embodiments, a portion of the second dilution 203 may then be transferred 209 to begin creation of a third dilution 205. Additional diluent may be added to the third dilution 205 to achieve an even less concentrated dilution. The dilutions may be added to one or more topical application media (including and without limitation one or more of emulsion cream bases, gel bases, or oil bases) to form an immunotherapy topical application compound via any method by which a dilution may be added to a topical application medium, for example and without limitation, syringe-to-syringe, an electronic method such as an electric mortar and pestle (commonly known in the art as an "EMP"), or by hand with a traditional mortar and pestle or ointment slab. Two example dilution series are provided below. In the following examples, note that multiple allergens may be used simultaneously and may act as diluent with respect to other allergens; for example and without limitation, if the requisite ratio were 0.1 mL of an allergen with 1.9 mL of a diluent, 12 allergens of 0.1 mL each could be mixed with 0.8 mL of a diluent; in this way, each allergen would make up 1/20 of the total compound. Though the below examples only discuss mixing one allergen at a time, compounds using multiple allergens simultaneously fall well within the scope of this disclosure, including compounds with a sufficient number of distinct allergens such that no traditional diluent is needed (in the prior example, a compound with twenty different allergens would not need a traditional diluent). Further, though the below examples discuss creams, note that similar embodiments using one or more creams, gels, or oils fall within the scope of the present disclosure.

In one or more embodiments, 0.1 mL of an allergen may be mixed with 1.9 mL of a diluent to form a first dilution 201 totaling 2 mL and bearing a ratio of one-part allergen per twenty parts of the first dilution 201. In one or more embodiments, 0.4 mL may be transferred 207 from the first dilution 201 to begin creation of the second dilution 203. 1.6 mL of diluent may be added to the transferred 0.4 mL to form a second dilution 203 totaling 2 mL and bearing a ratio of one-part allergen per one hundred parts of the second dilution 203. In one or more embodiments, 0.4 mL may be transferred 209 from the second dilution 203 to begin creation of the third dilution 205. 1.6 mL of diluent may be added to the transferred 0.4 mL to form a third dilution 205 totaling 2 mL and bearing a ratio of one-part allergen per five hundred parts of the dilution. In one or more embodiments, 0.8 mL of the third dilution 205 may be mixed with 3.2 mL of cream to form an immunotherapy cream for application during a first month; this exemplary immunotherapy cream would have a total volume of 4 mL and a ratio of one part allergen per 2,500 parts immunotherapy cream. In one or more embodiments, 0.8 mL of the second dilution 203 may be mixed with 3.2 mL of cream to form an immunotherapy cream for application during a second month; this exemplary immunotherapy cream would have a total volume of 4 mL and a ratio of one part allergen per five hundred parts immunotherapy cream. In one or more embodiments, 0.8 mL of the first dilution 201 may be mixed with 3.2 mL of cream to form an immunotherapy cream for application during a third month; this exemplary immunotherapy cream would have a total volume of 4 mL and a ratio of one part allergen per one hundred parts immunotherapy cream. In one or more embodiments, a maintenance cream may be formed by combining 2 mL of the first dilution 201 with 8 mL of the cream for application following the third month; this exemplary immunotherapy cream would have a total volume of 10 mL and a ratio of one part allergen per one hundred parts immunotherapy cream. In one or more embodiments, any dilution that remains after forming a cream may be saved for the next time cream is formed. The above exemplary dilution series may be suitable for animals weighing equal to or more than twenty pounds. Those skilled in the art will understand that the above example is purely exemplary and that the present invention may be practiced via any concentration and/or quantity of diluent, allergen, and cream.

As another example, in one or more embodiments, 0.05 mL of an allergen may be mixed with 4.95 mL of diluent to form a first dilution 201 totaling 5 mL and bearing a ratio of one-part allergen per one hundred parts of the first dilution 201. In one or more embodiments, 0.4 mL may be transferred 207 from the first dilution 201 to begin creation of the second dilution 203. 1.6 mL of diluent may be added to the transferred 0.4 mL to form a second dilution 203 totaling 2 mL and bearing a ratio of one-part allergen per five hundred parts of the second dilution 203. In one or more embodiments, 0.4 mL may be transferred 209 from the second dilution 203 to begin creation of the third dilution 205. 1.6 mL of diluent may be added to the transferred 0.4 mL to form a third dilution 205 totaling 2 mL and bearing a ratio of one-part allergen per 2,500 parts of the dilution. In one or more embodiments, 0.8 mL of the third dilution 205 may be mixed with 3.2 mL of cream to form an immunotherapy cream for application during a first month; this exemplary immunotherapy cream would have a total volume of 4 mL and a ratio of one part allergen per 12,500 parts immunotherapy cream. In one or more embodiments, 0.8 mL of the second dilution 203 may be mixed with 3.2 mL of cream to form an immunotherapy cream for application during a second month; this exemplary immunotherapy cream would have a total volume of 4 mL and a ratio of one part allergen per 2,500 parts immunotherapy cream. In one or more embodiments, 0.8 mL of the first dilution 201 may be mixed with 3.2 mL of cream to form an immunotherapy cream for application during a third month; this exemplary immunotherapy cream would have a total volume of 4 mL and a ratio of one part allergen per five hundred parts immunotherapy cream. In one or more embodiments, a maintenance cream may be formed by combining 2 mL of the first dilution 201 with 8 mL of the cream for application following the third month; this exemplary immunotherapy cream would have a total volume of 10 mL and a ratio of one part allergen per five hundred parts immunotherapy cream. In one or more embodiments, any dilution that remains after forming a cream may be saved for the next time cream is formed. The above exemplary dilution series may be suitable for animals weighing less than twenty pounds. Those skilled in the art will understand that the above example is purely exemplary and that the present invention may be practiced via any concentration and/or quantity of diluent, allergen, and cream.

The topical application compound should be regularly delivered to the animal dermally or transdermally. In one or more embodiments, the topical application compound may be applied daily. In one or more embodiments, a first topical application compound may be applied daily for a first month, a second topical application compound may be applied daily for a second month, a third topical application compound may be applied daily for a third month, and a maintenance topical application compound may be applied daily and perpetually after the third month. As the animal's immune system becomes less sensitive to the allergen, more allergen can be safely applied to expedite desensitization. Thus, in many embodiments, the first topical application compound may include the lowest total amount of allergen, the second topical application compound may include more allergen than the first topical application compound, the third topical application compound may include more allergen than the second topical application compound, and the maintenance topical application compound may include the most allergen. This is just one exemplary schedule that may be used to practice the present invention; any suitable administration schedule may be used.

Figure 3:
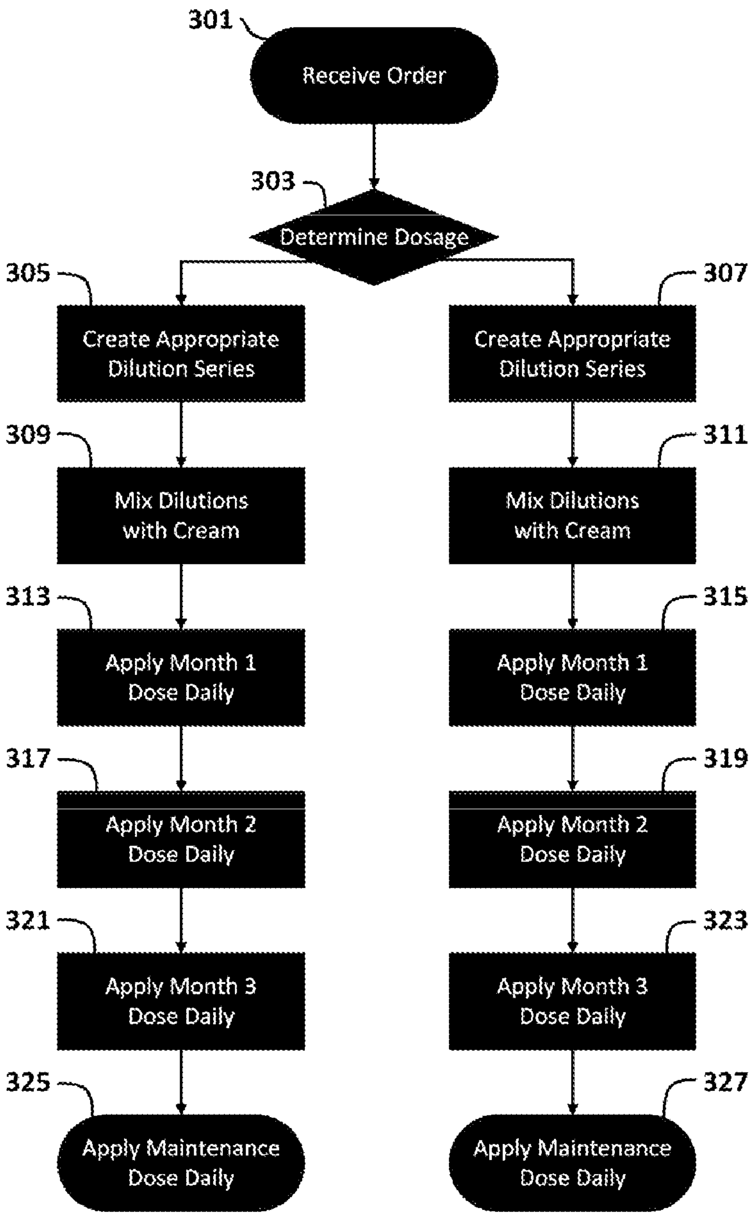
FIG. 3 depicts an exemplary flow diagram illustrating a method for creating and administering a dermal or transdermal immunotherapy topical application compound, according to one or more aspects of the present disclosure.

FIG. 3 depicts an exemplary flow diagram illustrating a method for creating and administering a dermal or transdermal immunotherapy cream, according to one or more aspects of the present disclosure. Though a cream is discussed in FIG. 3, embodiments using any form of one or more topical application compounds (including and without limitation any cream, gel, or oil) are well within the scope of this disclosure. In one or more embodiments, a veterinarian, pharmacist, or other animal care provider may receive an order 301. The order 301 may include one or more of the animal's species, breed, weight, gender, one or more allergies, or one or more medical conditions. The information from the order 301 may be used to determine one or more suitable dosages 303—that is, one or more combinations of suitable concentration and quantity of allergen to be applied to the animal per unit of time. In one or more embodiments, the dosage 303 may increase regularly over time until a maintenance dosage is reached 325 and 327. In one or more embodiments, it may be desirable to separate the dosage amounts 303 based on the animal's weight. For example and without limitation, it may be desirable to have one predetermined sequence of dosages 303 for animals under twenty pounds and a different predetermined sequence of dosages 303 for animals over twenty pounds. In one or more embodiments, the dosages 303 may be created via a dilution series 305 and 307 as depicted in FIG. 2. FIG. 3 depicts two possible dilution series options 305 and 307, but those skilled in the art will understand that any number of dilution series options 305 and 307 or other dosage options 303 falls within the scope of the invention.

Once an appropriate dilution series 305 and 307 is created based on an animal's order 301, a mixture of diluent and allergen may be mixed with a topical application medium such as a gel, oil, or cream 309 and 311. The topical application compound produced from the combination of the diluent, allergen, and topical application medium may then be applied to the animal's skin or inner ear regularly 313 and 315. In one or more embodiments, a first dosage may be applied for a first month 313 and 315, a second dosage may be applied for a second month 317 and 319, a third dosage may be applied for a third month 321 and 323, and a maintenance dosage may be applied indefinitely 325 and 327 after the third month. Though FIG. 3 depicts three month-long dosages followed by a maintenance dose, the present invention may be administered via any number of successive dosages lasting any suitable length of time. In one or more embodiments, the topical application compound may be applied daily. In other embodiments, the topical application compound may be applied across other regular units of time, including and without limitation three times a day, twice a day, once every two days, or weekly.

Figure 4:
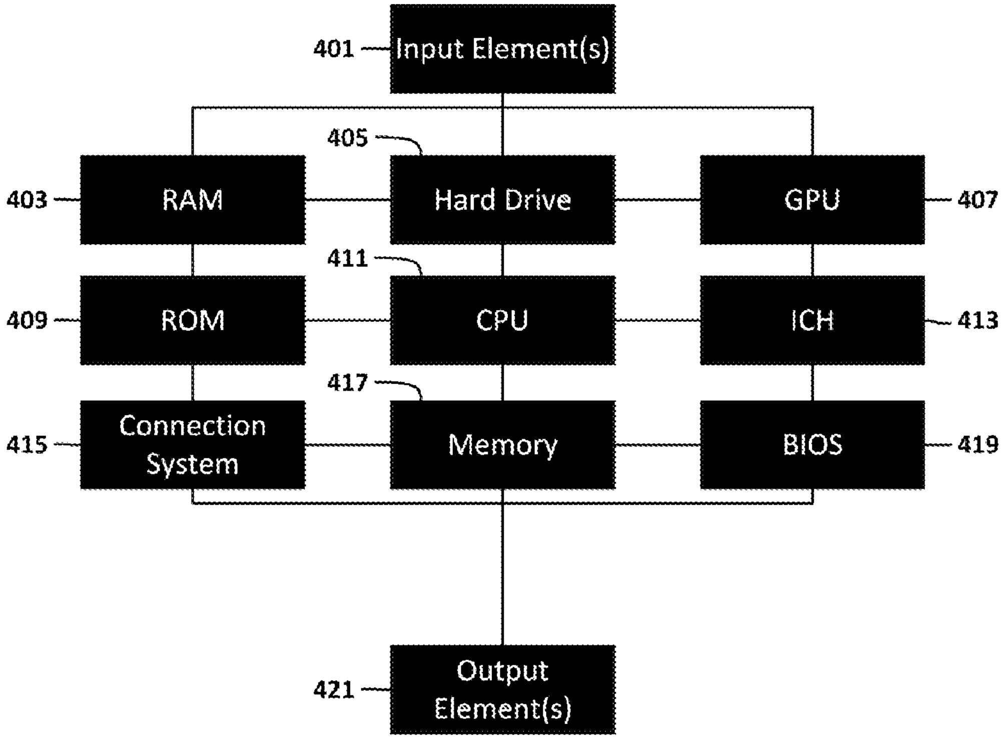
FIG. 4 depicts a schematic diagram of an information handling system for use with the production and administration of medication, according to one or more aspects of the present disclosure.

FIG. 4 depicts a schematic diagram of an information handling system for use with the production and administration of medication, according to one or more aspects of the present disclosure. In one or more embodiments, the present invention may be practiced in combination with an information handling system, including one or more of a hard drive 405, a GPU 407, a CPU 411, a connection system 415, a Basic Input/Output System (BIOS) 419, an Input/Output Controller Hub (ICH) 413, memory 417, RAM 403, ROM 409, an input element 401, an output element 421, and any multiple thereof (for example and without limitation, two hard drives). The input elements 401 may include one or more of a keyboard, a mouse, a touch screen, or other input elements. The output elements 421 may include one or more of a monitor, a speaker, or other output elements. The connection system 415 may be any means to connect to an external system, including and without limitation via the Internet, an intranet, or a local connection. Further, the connection system 409 may be wired, wireless, or any combination thereof. The CPU 411 may be any kind of processor, including and without limitation one or more microcontrollers, microprocessors, embedded processors, or digital signal processors.

In one or more embodiments, the disclosed systems and methods for producing and administering dermal and transdermal immunotherapy topical application compounds to animals may incorporate an information handling system in one or more ways. For example and without limitation, a hard drive 405 or other memory 417 storing device may store data about animal patients, for example and without limitation, one or more dosing schedules, prescriptions, orders, allergies, weights, species, breeds, genders, or medical conditions. In some embodiments, one or more processors 411 may use information from one or more input elements 401 to calculate one or more dosing schedules, including one or more dates, concentrations, or quantities for administration of immunotherapy topical application compounds. Data produced by one or more processors 411 may be communicated to a user via one or more output elements 421. In one or more embodiments, an information handling system may connect to external devices via one or more of a wired or wireless connection. In one or more embodiments, an information handling system may send one or more signals to control one or more pieces of hardware (for example and without limitation, a dispenser of topical application media). An information handling system may access information, including and without limitation one or more of animal patient records data or allergen data, from an outside source via one or more connection systems 415. Similarly, an information handling system may upload information, including and without limitation one or more of animal patient records data or allergen data, to an outside source via one or more connection systems 415.

The elements of FIG. 4 may be added, omitted, or changed in any combination without departing from the scope of the present disclosure. One or more elements of FIG. 4 may be physical, logical, or any combination thereof. FIG. 4 depicts one exemplary information handling system; however, any information handling system including one or more elements from FIG. 4 may be used to practice the present invention.

An embodiment of the present disclosure is a method for treating an allergy condition of an animal, comprising: detecting that the animal has the allergy condition; determining a first quantity of a topical application medium and a first quantity of an allergen based at least in part on one or more attributes of the animal; providing a first topical application compound, the first topical application compound comprising the first quantity of the allergen and the first quantity of the topical application medium; and applying the first topical application compound to one or more ears of the animal one or more times to treat the allergy condition.

In one or more embodiments, the first topical application compound may be applied to one or more pinnae of one or more ears. In one or more embodiments, the animal may be a dog or a cat. In one or more embodiments, the attributes of the animal may comprise one or more of a weight, a species, a breed, a gender, a preexisting condition, or an allergy diagnosis of the animal. In one or more embodiments, the allergy condition may comprise atopic dermatitis. In one or more embodiments, the first quantity of the topical application medium and the first quantity of the allergen may be determined at least in part based on information from an information handling system. In one or more embodiments, the first topical application compound may be applied to one or more ears of the animal by: inserting at least the first topical application compound into an emulsion pen; holding an ejecting end of the emulsion pen near or against the one or more ears of the animal; actuating the emulsion pen to emit the first topical application compound from the ejecting end; and rubbing the first topical application compound against the one or more ears of the animal. In one or more embodiments, the method for treating an allergy condition of an animal may further comprise: determining a second quantity of the topical application medium and a second quantity of the allergen; providing a second topical application compound comprising the second quantity of the topical application medium and the second quantity of the allergen; and applying the second topical application compound to one or more ears of the animal one or more times. In one or more embodiments, the first topical application compound may be applied at regular time intervals for a first predetermined period of time, and the second topical application compound may subsequently be applied at the regular time intervals for a second predetermined period of time. In one or more embodiments, the second quantity of the allergen may be greater than the first quantity of the allergen.

An embodiment of the present disclosure is a method for treating an allergy condition of an animal, comprising: detecting that the animal has the allergy condition; determining a first quantity of a topical application medium and a first quantity of an allergen based at least in part on one or more attributes of the animal; providing a first topical application compound comprising the first quantity of the topical application medium and the first quantity of the allergen; affixing an Elizabethan collar to a neck or a head of the animal; and applying the first topical application compound to one or more locations on the animal's skin one or more times.

In one or more embodiments, the topical application compound may be applied to the one or more locations on the animal's skin by inserting at least the first topical application compound into an emulsion pen; holding an ejecting end of the emulsion pen near or against the one or more locations on the animal's skin; actuating the emulsion pen to emit the first topical application compound out of the ejecting end; and rubbing the first topical application compound against the animal's skin. In one or more embodiments, the method for treating an allergy condition of an animal may further comprise determining a second quantity of the topical application medium and a second quantity of the allergen; providing a second topical application compound, comprising the second quantity of the topical application medium and the second quantity of the allergen; and applying the second topical application compound to one or more locations on the animal's skin one or more times. In one or more embodiments, the first topical application compound may be applied at regular intervals for a first predetermined period of time, and the second topical application compound may subsequently be applied at the regular time intervals for a second predetermined period of time.

An embodiment of the present disclosure is a system, comprising: a topical application compound capable of treating an allergy condition of an animal via dermal or transdermal application of the topical application compound comprising an allergen and a topical application medium; a cylindrical body holding the topical application compound; and an opening disposed upon an end of the cylindrical body through which the topical application compound may exit the ejection tube.

In one or more embodiments, the topical application compound may further comprise a diluent. In one or more embodiments, the ejection tube may be an emulsion pen, a micro-pen, or a syringe. In one or more embodiments, one or more of a quantity of the diluent, a quantity of the allergen, and a quantity of the topical application medium may be determined based on one or more of a weight, a species, a breed, a gender, a preexisting condition, or an allergy diagnosis of the animal. In one or more embodiments, the diluent may comprise one or more of human serum albumin, sterile water, sterile water with phenol, or 50% glycerin. In one or more embodiments, the system may further comprise an information handling system, the information handling system comprising: an output system comprising one or more of a screen or a speaker; a non-transitory computer readable medium for storing instructions; and a processor that executes the instructions from the non-transitory computer readable medium, causing the processor to: determine a quantity of the topical application medium and a quantity of the allergen based at least in part on one or more attributes of an animal; and cause the output system to provide information about one or more of the quantity of the topical application medium and the quantity of the allergen to a user.

While the present disclosure has been described in connection with presently preferred embodiments, it will be understood by those skilled in the art that it is not intended to limit the disclosure to those embodiments. It is therefore contemplated that various alternative embodiments and modifications may be made to the disclosed embodiments without departing from the spirit and scope of the disclosure defined by the appended claims and equivalents thereof. In particular, with regard to the methods disclosed, one or more steps may not be required in all embodiments of the methods and the steps disclosed in the methods may be performed in a different order than was described. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (for example, "from about a to about b," or, equivalently, "from approximately a to b," or, equivalently, "from approximately a-b") disclosed herein is to be understood as referring to the power set (the set of all subsets) of the respective range of values. Furthermore, the words "comprising" (and any form of comprising, such as "comprise" and "comprises"), "having" (and any form of having, such as "has" and "have"), "including" (and any form of including, such as "includes" and "include") or "containing" (and any form of containing, such as "contains" and "contain") are to be understood as inclusive or open-ended and do not exclude additional, unrecited elements or method steps. The word "some" is to be understood as meaning "one or more." The terms "topical application compound," "topical application medium," and the plural forms of those terms are used herein as umbrella terms for pharmaceutical bases by which allergens may be applied to the skin of an animal for absorption to the immune systems, including and without limitation all forms of creams, gels, and oils whether administered dermally or transdermally; the terms "topical application compound," "topical application medium," and the plural forms of those terms should be understood to include combinations comprising (1) one or more media and one or more allergen and (2) one or more media without an allergen yet inserted. Further, the terms "topical application compound, "topical application medium," and the plural forms of those terms include homogenous and non-homogenous media. The terms "dog" and "dogs" are used herein to mean any one or more canines owned, domesticated, or cared for by one or more humans. Similarly, the terms "cat" and "cats" are used herein to mean any one or more felines owned, domesticated, or cared for by one or more humans. The term "coupled" should be understood to include any connection between two things, including and without limitation a physical connection (including and without limitation a wired connection), a non-physical connection (including and without limitation a wireless connection), or any combination thereof. The terms in the claims have their plain, ordinary meaning unless otherwise explicitly and clearly defined by the patentee.

What is claimed is:

1. A method for treating an allergy condition of an animal, comprising:

detecting that the animal has the allergy condition;

determining a first quantity of a topical application medium and a first quantity of an allergen based at least in part on one or more attributes of the animal;

providing a first topical application compound, the first topical application compound comprising:

the first quantity of the allergen; and the first quantity of the topical application medium; and applying the first topical application compound to one or more ears of the animal one or more times to treat the allergy condition, wherein the first topical application compound is applied to the one or more ears of the animal by:

inserting at least the first topical application compound into an emulsion pen;

holding an ejecting end of the emulsion pen near or against the one or more ears of the animal;

actuating the emulsion pen to emit the first topical application compound from the ejecting end; and rubbing the first topical application compound against the one or more ears of the animal.

2. The method of claim 1, wherein the first topical application compound is applied to one or more pinnae of the one or more ears.

3. The method of claim 1, wherein the animal is a dog or a cat.

4. The method of claim 1, wherein the one or more attributes of the animal comprises one or more of a weight, a species, a breed, a gender, a preexisting condition, or an allergy diagnosis of the animal.

5. The method of claim 1, wherein the allergy condition comprises atopic dermatitis.

6. The method of claim 1, wherein the first quantity of the topical application medium and the first quantity of the allergen are determined at least in part based on information from an information handling system.

7. The method of claim 1, further comprising:

determining a second quantity of the topical application medium and a second quantity of the allergen;

providing a second topical application compound, comprising:

the second quantity of the topical application medium; and the second quantity of the allergen; and applying the second topical application compound to the one or more ears of the animal one or more times.

8. The method of claim 7, wherein the first topical application compound is applied at regular time intervals for a first predetermined period of time, and the second topical application compound is subsequently applied at the regular time intervals for a second predetermined period of time.

9. The method of claim 8, wherein the second quantity of the allergen is greater than the first quantity of the allergen.

10. A method for treating an allergy condition of an animal, comprising:

detecting that the animal has the allergy condition;

determining a first quantity of a topical application medium and a first quantity of an allergen based at least in part on one or more attributes of the animal;

providing a first topical application compound, comprising:

the first quantity of the topical application medium; and the first quantity of the allergen;

affixing an Elizabethan collar to a neck or a head of the animal; and applying the first topical application compound to one or more locations on the animal's skin one or more times, wherein the first topical application compound is applied to the one or more locations on the animal's skin by:

inserting at least the first topical application compound into an emulsion pen;

holding an ejecting end of the emulsion pen near or against the one or more locations on the animal's skin;

actuating the emulsion pen to emit the first topical application compound out of the ejecting end; and rubbing the first topical application compound against the animal's skin.

11. The method of claim 10, further comprising:

determining a second quantity of the topical application medium and a second quantity of the allergen;

providing a second topical application compound, comprising:

the second quantity of the topical application medium; and the second quantity of the allergen; and applying the second topical application compound to the one or more locations on the animal's skin one or more times.

12. The method of claim 11, wherein the first topical application compound is applied at regular intervals for a first predetermined period of time, and the second topical application compound is subsequently applied at the regular time intervals for a second predetermined period of time.

13. The method of claim 1, wherein the topical application medium comprises a cream, and wherein the allergen is associated with the allergy condition of atopic dermatitis.

14. The method of claim 10, wherein the topical application medium comprises a cream, and wherein the allergen is associated with the allergy condition of atopic dermatitis.

* * * * *